United States Patent
Horn et al.

(10) Patent No.: US 11,926,168 B2
(45) Date of Patent: Mar. 12, 2024

(54) NON-PHENOLIC COLOR DEVELOPER AND HEAT-SENSITIVE RECORDING MATERIAL

(71) Applicant: Papierfabrik August Koehler SE, Oberkirch (DE)

(72) Inventors: Michael Horn, Offenburg (DE); Timo Stalling, Appenweier (DE); Maren Steppat, Oberkirch (DE)

(73) Assignee: PAPIERFABRIK AUGUST KOEHLER SE, Oberkirch (DE)

( * ) Notice: Subject to any disclaimer, the term of this patent is extended or adjusted under 35 U.S.C. 154(b) by 581 days.

(21) Appl. No.: 16/615,439

(22) PCT Filed: May 17, 2018

(86) PCT No.: PCT/EP2018/062909
§ 371 (c)(1),
(2) Date: Nov. 21, 2019

(87) PCT Pub. No.: WO2018/215287
PCT Pub. Date: Nov. 29, 2018

(65) Prior Publication Data
US 2020/0172477 A1    Jun. 4, 2020

(30) Foreign Application Priority Data
May 24, 2017    (DE) .................. 10 2017 111 439.4

(51) Int. Cl.
| | |
|---|---|
| *B41M 5/333* | (2006.01) |
| *B41M 5/327* | (2006.01) |
| *B41M 5/337* | (2006.01) |
| *C07C 311/60* | (2006.01) |

(52) U.S. Cl.
CPC ........ *B41M 5/3333* (2013.01); *B41M 5/3375* (2013.01); *C07C 311/60* (2013.01); *B41M 5/3275* (2013.01)

(58) Field of Classification Search
CPC ... B41M 5/333; B41M 5/3333; B41M 5/3375
See application file for complete search history.

(56) References Cited

U.S. PATENT DOCUMENTS

| | | |
|---|---|---|
| 6,624,117 B1 | 9/2003 | Heneghan et al. |
| 2006/0004197 A1 | 1/2006 | Thrash et al. |
| 2009/0082202 A1 * | 3/2009 | Stork .................. B41M 5/3275 503/217 |

FOREIGN PATENT DOCUMENTS

| | | |
|---|---|---|
| CN | 1330593 A | 1/2002 |
| DE | 10196052 T1 | 2/2003 |
| EP | 0 526 072 A1 | 2/1993 |
| EP | 0 535 887 A1 | 4/1993 |
| EP | 0 542 556 A1 | 5/1993 |
| EP | 0 610 653 A1 | 8/1994 |
| EP | 0 620 122 A1 | 10/1994 |
| EP | 0 604 832 B1 | 6/1998 |
| EP | 1 044 824 A2 | 10/2000 |
| EP | 2 923 851 A1 | 9/2015 |
| JP | 6-64335 A | 3/1994 |
| JP | 09-58242 A | 3/1997 |
| JP | 11-263067 A | 9/1999 |
| JP | 11-268422 A | 10/1999 |
| WO | 00/35679 A1 | 6/2000 |
| WO | 20010072527 A1 | 10/2001 |
| WO | 20030074285 A1 | 9/2003 |

OTHER PUBLICATIONS

Howbert et al . . . "Novel agents effective against solid tumors: the diarylsulfonylureas. Synthesis, activities, and analysis of quantitative structure-activity relationship", J. Med. Chem., 1990, 33, p. 2393-2407 (Year: 1990).*
Office Action for Japanese Application No. 2019-564895, dated Aug. 27, 2021, 4 pages.
Office Action for Chinese Application No. 201880033903.6, dated Feb. 9, 2021, 15 pages.
Office Action for Korean Application No. 10-2019-7035444, dated Feb. 3, 2021, 17 pages.
Office Action for Chinese Application No. 201880033903.6, dated Jun. 28, 2021, 4 pages.
Office Action for Chinese Application No. 201880033903.6, dated Nov. 11, 2021, 4 pages.

* cited by examiner

*Primary Examiner* — Gerard Higgins
(74) *Attorney, Agent, or Firm* — Lippes Mathias LLP

(57) ABSTRACT

The invention relates to a color developer of formula (I), $(Ar^1-SO_2-NH-)_m-Y-(-NH-C(O)-NH-SO_2-Ar_2)_n$ (I), wherein $Ar^1$ is an unsubstituted or substituted aromatic moiety, $Ar^2$ is an unsubstituted or substituted phenyl moiety, Y is at least an (m+n)-times substituted benzene group or naphthalene group, and Y is substituted in such a way that at least one $Ar_2-SO_2-NH-C(O)-NH$ group is in ortho-position with respect to at least one $Ar^1-SO_2-NH$ group. The invention further relates to a heat-sensitive recording material, comprising a carrier substrate and a heat-sensitive color-forming layer, which contains at least one color former and at least one phenol-free color developer, the at least one color developer being the compound of formula (I). The invention further relates to a method for producing said heat-sensitive recording material.

10 Claims, No Drawings

NON-PHENOLIC COLOR DEVELOPER AND HEAT-SENSITIVE RECORDING MATERIAL

This application is a National Stage Entry of International Application No. PCT/EP2018/062909, filed May 17, 2018 and titled "NON-PHENOLIC COLOR DEVELOPER AND HEAT-SENSITIVE RECORDING MATERIAL", which claims priority of German Application No. 10 2017 111 439.4, filed May 24, 2017 and titled "NON-PHENOLIC COLOR DEVELOPER AND HEAT-SENSITIVE RECORDING MATERIAL". Both of which are incorporated herein by reference in their entireties.

The invention relates to a colour developer, a heat-sensitive recording material comprising a carrier substrate, and a heat-sensitive colour-forming layer, which contains at least one colour former and at least one phenol-free colour developer, and a method for production of same.

Heat-sensitive recording materials for direct thermal printing which have a heat-sensitive colour-forming layer (thermal reaction layer) applied to a carrier substrate have long been known. A colour former and a colour developer are usually present in the heat-sensitive colour-forming layer and react with one another under the action of heat and thus lead to a development of colour. (Bis)phenol colour developers are often used. Also known are heat-sensitive recording materials which contain a non-phenolic colour developer in the heat-sensitive colour-forming layer. These materials were developed in order to improve the resistance of the printed text, especially also when the printed heat-sensitive recording material is stored over a longer time or comes into contact with hydrophobic substances, such as plasticiser-containing materials or oils. Especially against the background of public discussions regarding the toxic potential of (bis)phenol chemicals, the interest in non-phenolic colour developers has increased greatly. In this regard the objective has been to avoid the toxicological disadvantages of the phenolic colour developers, however the technical performance properties that can be attained with phenolic colour developers should at least be maintained, and preferably enhanced.

Common structural features can be identified from the prior art with regard to non-phenolic colour developers, in spite of the broad chemical diversity of these materials.

Thus, a 1,3-disubstituted ureido substructure (Y—NH—CO—NH—Z) is a common feature of numerous non-phenolic colour developers. By appropriate selection of the groups Y and Z it is possible to modulate the functional properties relevant for suitability as a colour developer.

Colour developers with sulfonyl-urea structures (—SO$_2$—NH—CO—NH—) are widespread since they can be produced relatively easily and the heat-sensitive recording materials produced with their use have good application properties.

EP 0 526 072 A1 discloses colour developers from of formula the class of aromatic sulfonyl-(thio)urea compounds of formula

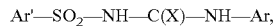

Ar'—SO$_2$—NH—C(X)—NH—Ar, wherein X=O or S, and Ar and Ar' are aromatic groups.

These colour developers can be used to produce heat-sensitive recording materials that are characterised by an improved text permanence. The heat-sensitive recording materials based on these colour developers also have a usable thermal print sensitivity with good surface whiteness, such that, with appropriate composition of the formulation of the heat-sensitive colour-forming layer, it is relatively easy to produce high print densities with use of commercially available thermal printers.

WO 0 035 679 A1 discloses aromatic and heteroaromatic sulfonyl-(thio)urea compounds (X=S or O) and/or sulfonyl guanidines (X=NH) of the above formula, wherein Ar is linked to further aromatic groups by a divalent linker group. A non-phenolic colour developer from this class that is widely used in practice, 4-methyl-N—(((3-(((4-methylphenyl)sulfonyl)oxy)phenyl)amino) carbonyl)benzenesulfonamide (trade name Pergafast 201®, BASF), is characterised by the balance of the application properties of the heat-sensitive recording materials produced with this colour developer. Especially, they have a good dynamic response sensitivity and an acceptable resistance of the print to hydrophobic substances.

Sulfonyl urea units connected via a divalent or polyvalent linker group A, for example bis-sulfonyl urea compounds of formula (Ar—SO$_2$—NH—C(O)—NH—)$_2$A, wherein Ar is an aromatic group, have also been described many times over as colour developers (see EP 0 535 887 A1, EP 0 542 556 A1, EP 0 604 832 B1, EP 0 620 122 A1 and EP 1 044 824 A2).

In practice, N,N'-(methylenebis(4,1-phenyleneiminocarbonyl))bis(4-methyl-benzenesulfonamide) (B-TUM) above all has established itself (A=CH$_2$, Ar=4-methylphenyl).

The combination of a sulfonyl urea structure with an N-sulfonyl(thio)urethane group of formula

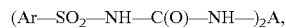

(Ar—SO$_2$—NH—C(O)—NH—)$_n$(Ar—SO$_2$—NH—C(O)—X—)$_m$A, wherein Ar is an aromatic group, A is an (m+n)valent organic linker group, and X=O or S, is the subject of JP H 0 664 335.

An increased resistance of the printed text compared to hydrophobic agents has been described for the heat-sensitive recording materials produced using these colour developers. However, the synthetic access to these colour developers is problematic especially if chemically uniform substances are desired.

JP H 0 958 242 combines sulfonyl resin substructures with primary sulfonamide groups in order to obtain colour developers of formula

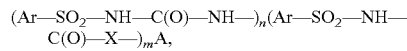

R—SO$_2$—NH—C(X)—NH—C$_6$H$_4$—SO$_2$—NH$_2$.

JP H 11-263067 discloses colour developers formed from (thio)urea and sulfonyl(thio)urea substructures, linked via an aromatic linker unit, of formula

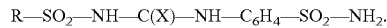

Ar$^1$—NH—C(X)—NH-A-SO$_2$—NH—C(X)—NH—Ar$^2$,

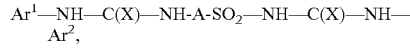

wherein X=O or S, and Ar$^1$ and Ar$^2$ are aromatic groups.

A common feature of the heat-sensitive recording materials based on sulfonylurea chemistry and obtained with non-phenolic colour developers is that they demonstrate good levels of performance in respect of some application-relevant properties, but display weaknesses in respect of other properties.

For example, a high resistance of the print to hydrophobic substances is often associated with a moderate response sensitivity (dynamic sensitivity) in the thermal printer, which can be effectively improved only by using large amounts of partly quite specific melt auxiliaries (specific thermal solvents or specific sensitising agents).

On the other hand, high dynamic sensitivity values can be easily achieved with certain non-phenolic colour developers, wherein, however, the resistance of the printed text is only moderate. This defect can be overcome with the aid of ageing inhibitors (stabilisers), however this is at the cost of a more complex and more costly formulation of the recording layer.

The aim of the present invention is therefore to overcome the above-described disadvantages of the prior art. Especially, the aim of the present invention is to provide a heat-sensitive recording material which has a high dynamic sensitivity (high response sensitivity in the thermal printer) and, in respect of other application-relevant performance features, achieves at least the level of the recording materials based on non-phenolic colour developers of the prior art, without being reliant on specific formulation components in the heat-sensitive functional layer, such as ageing inhibitors or specific melt auxiliaries, which have limited availability and are costly. A primary aim of the present invention was to provide colour developers which enable a high print density of the image, without any undesirable effects on the starting temperature (static sensitivity) of the recording material. At the same time a good resistance of the printed text of the heat-sensitive recording material especially to hydrophobic agents should be achieved, as compared to the prior art.

This aim is addressed in accordance with the invention by the use of a compound according to claim 1 in a heat-sensitive recording material according to claim 9.

It has surprisingly been found that it is possible, with colour developers of the specific substitution pattern of formula (I), to attain heat-sensitive recording materials which are characterised by a high dynamic sensitivity and which cannot be produced with comparable formulations for a heat-sensitive recording material with other substitution patterns of the colour developer of the same chemical compound class. The recording materials produced with the colour developers according to the invention also have a good resistance of the printed text compared to hydrophobic agents, corresponding at least to that of the prior art.

The compound according to claim 1 has the formula (I)

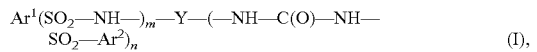

$$Ar^1(SO_2-NH-)_m-Y-(-NH-C(O)-NH-SO_2-Ar^2)_n \qquad (I),$$

wherein $Ar^1$ is an unsubstituted or substituted aromatic group, $Ar^2$ is an unsubstituted or substituted phenyl group, Y is at least one benzene group or naphthalene group substituted (m+n) times, and Y is substituted in such a way that at least one $Ar^2-SO_2-NH-C(O)-NH$ group is in the ortho position, i.e. in the 1,2 position, with respect to at least one $Ar^1-SO_2-NH$ group.

Preferably, m is equal to 1 and n is greater than or equal to 1.

Preferably, n is equal to 1 and m is 1 or 2.

Preferably, $Ar^1$ is an unsubstituted or substituted phenyl group or an unsubstituted or substituted 2-naphthyl group.

Especially preferably, $Ar^1$ is an unsubstituted phenyl or a monosubstituted phenyl group.

The monosubstituted phenyl group is preferably substituted with a $C_1$-$C_5$ alkyl, an alkenyl, an alkynyl, a benzyl, an RO, a halogen, a formyl, an ROC, an $RO_2C$, a CN, an $NO_2$, an $R-SO_2O$, an $RO-SO_2$, an $R-NH-SO_2$, an $R-SO_2-NH$, an $R-NH-CO-NH$, an $R-SO_2-NH-CO-NH$, an $R-NH-CO-NH-SO_2$ or an $R-CO-NH$ group, wherein R is a $C_1$-$C_5$ alkyl, an alkenyl, an alkynyl, a phenyl, a tolyl or a benzyl group, preferably a phenyl or a p-tolyl group.

Preferred substituents are $C_1$-$C_5$ alkyl, RO, halogen, $RO_2C$, $R-SO_2O$, $R-NH-CO-NH$ and $R-SO_2-NH-CO-NH$ groups.

Preferably, $Ar^2$ is an unsubstituted phenyl group or a monosubstituted phenyl group, especially a phenyl group substituted with a $C_1$-$C_4$ alkyl group, especially preferably a phenyl group substituted with a methyl group.

In an especially preferred embodiment $Ar^1$ is an unsubstituted phenyl group or a monosubstituted phenyl group, $Ar^2$ is an unsubstituted phenyl group or a monosubstituted phenyl group, and Y is a benzene group substituted (m+n) times.

Especially preferred compounds of formula (I) are shown in the following Table 1.

TABLE 1

Preferred compounds of formula (I) with the stated meanings for the Y group, the $Ar^1$ group, the $Ar^2$ group, m and n (R = as mentioned above)

| | Y | $Ar^1$ | $Ar^2$ | m | n |
|---|---|---|---|---|---|
| I | Phenylene | phenyl | phenyl | 1 | 1 |
| II, XIV, XVII | Phenylene | phenyl | $C_1$-$C_4$ alkyl-substituted phenyl | 1 | 1 |
| III, XV, XVIII | Phenylene | $C_1$-$C_5$ alkyl-substituted phenyl | phenyl | 1 | 1 |
| IV, V, VI, XVI, XIX | Phenylene | $C_1$-$C_5$ alkyl-substituted phenyl | $C_1$-$C_4$ alkyl-substituted phenyl | 1 | 1 |
| VII | Phenylene | RO-substituted phenyl | $C_1$-$C_4$ alkyl-substituted phenyl | 1 | 1 |
| VIII | Phenylene | halogen-substituted phenyl | $C_1$-$C_4$ alkyl-substituted phenyl | 1 | 1 |
| IX | Phenylene | $R-CO-NH$-substituted phenyl | $C_1$-$C_4$ alkyl-substituted phenyl | 1 | 1 |
| X | Phenylene | nitro-substituted phenyl | $C_1$-$C_4$ alkyl-substituted phenyl | 1 | 1 |
| XI | Phenylene | $RO_2C$-substituted phenyl | $C_1$-$C_4$ alkyl-substituted phenyl | 1 | 1 |
| XII | Phenylene | naphthyl | $C_1$-$C_4$ alkyl-substituted phenyl | 1 | 1 |
| XIII | Phenylene | benzyl | $C_1$-$C_4$ alkyl-substituted phenyl | 1 | 1 |
| XXI | trisubstituted benzene | $C_1$-$C_5$ alkyl-substituted phenyl | phenyl | 1 | 2 |
| XX, XXII, XXIII, XXIV | trisubstituted benzene | $C_1$-$C_5$ alkyl-substituted phenyl | $C_1$-$C_4$ alkyl-substituted phenyl | 1 | 2 |

The compound of formula (I) according to the invention can be produced by methods known per se.

The following reaction scheme 1 shows a possible synthesis pathway for the compound of formula (I) according to the invention on the basis of the example of compounds I to XIX (see Table 2).

Reaction scheme 1

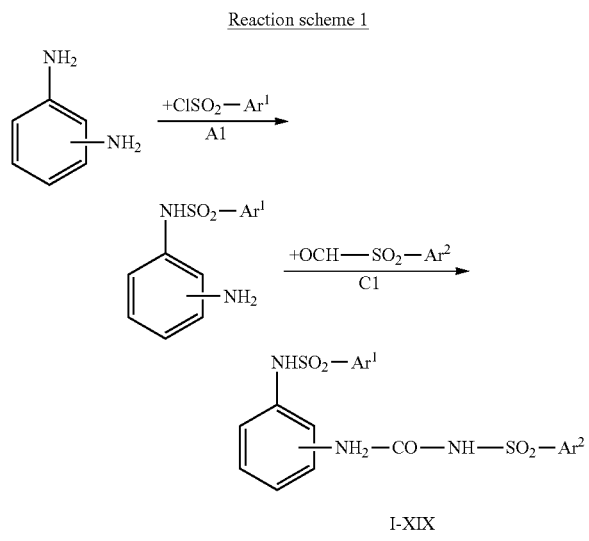

(Ar, Ar: see Table 2)

The following reaction scheme 2 shows a possible synthesis pathway for the compound of formula (I) according to the invention on the basis of the example of compounds XX to XXIV (see Table 2).

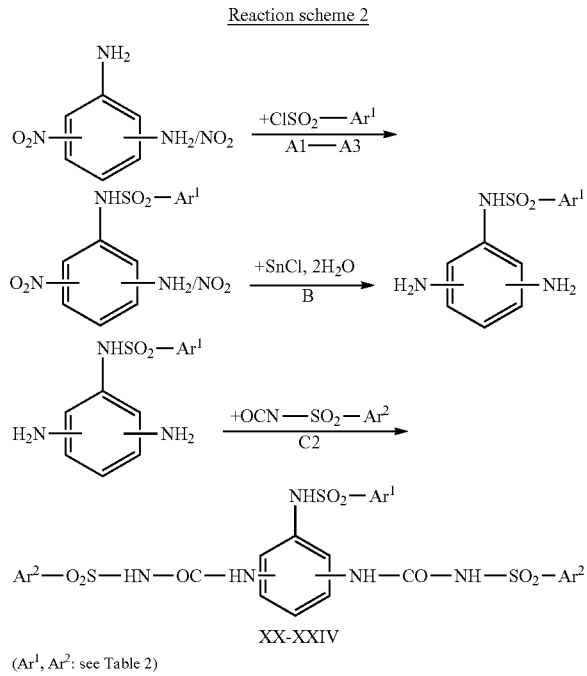

(Ar$^1$, Ar$^2$: see Table 2)

Reaction scheme 2 (Ar$^1$, Ar$^2$: see Table 2)

The compound XX falling under the compound of formula (I) according to the invention (see Table 2) can be produced starting from 2,6-dinitroaniline, which is firstly converted in accordance with the following reaction scheme 3 into 1,2-diamino-3-nitrobenzene (V. Milata, J. Salon, Org. Prep. Proceed. Int., 31 (3), 347 (1999)) and is then converted into the end product by the described methods.

Reaction scheme 3

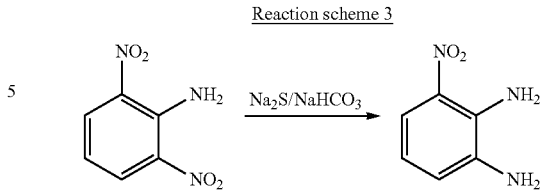

The preferred embodiments described in conjunction with the compound of formula (I) apply similarly for the method for production thereof.

As already mentioned, the present invention also relates to a heat-sensitive recording material comprising a carrier substrate, at least one colour former, and a heat-sensitive colour-forming layer containing phenol-free colour developer, wherein the at least one phenol-free colour developer is the compound of the above-described formula (I).

The compound of formula (I) is preferably present in an amount of from approximately 3 to approximately 35% by weight, especially preferably in an amount of from approximately 10 to approximately 25% by weight, in relation to the total solid content of the heat-sensitive layer.

The selection of the carrier substrate is not critical. However, it is preferred to use paper, synthetic paper, and/or a plastic film as carrier substrate.

At least one further intermediate layer is optionally provided between the carrier substrate and the heat-sensitive layer, wherein the purpose of this at least one further intermediate layer is to improve the surface smoothness of the carrier substrate for the heat-sensitive layer and to ensure a heat barrier between the carrier substrate and the heat-sensitive layer. Organic hollow bead pigments and/or calcined kaolins are preferably used in this intermediate layer. At least one protective layer and/or at least one layer promoting printability can also be provided in the heat-sensitive recording material according to the invention, wherein these layers can be applied on the front or rear side of the substrate.

With regard to the choice of the colour former, the present invention is also not subject to any major limitations. The colour former, however, is preferably a dye of the triphenylmethane type, of the fluorane type, of the azaphthalide type and/or of the fluorene type. A very especially preferred colour former is a dye of the fluorane type, since, thanks to its availability and balanced application-related properties, it is possible to provide a recording material having an attractive price-performance ratio.

Especially preferred dyes of the fluorane type are:
3-diethylamino-6-methyl-7-anilinofluorane,
3-(N-ethyl-N-p-toluidineamino)-6-methyl-7-anilinofluorane,
3-(N-ethyl-N-isoamylamino)-6-methyl-7-anilinofluorane,
3-diethylamino-6-methyl-7—(o,p-dimethylanilino)fluorane,
3-pyrrolidino-6-methyl-7-anilinofluorane,
3-(cyclohexyl-N-methylamino)-6-methyl-7-anilinofluorane,
3-diethylamino-7-(m-trifluoromethylanilino)fluorane,
3-N-n-dibutylamino-6-methyl-7-anilinofluorane,
3-diethylamino-6-methyl-7-(m-methylanilino)fluorane,
3-N-n-dibutylamino-7-(o-chloroanilino) fluorane,
3-(N-ethyl-N-tetrahydrofurfurylamine)-6-methyl-7-anilino-fluorane, 3-(N-methyl-N-propylamine)-6-methyl-7-anilinofluorane, 3-(N-ethyl-N-ethoxypropylamine)-6-methyl-7-anilinofluorane, 3-(N-ethyl-N-isobutylamine)-6-methyl-7-anilinofluorane and/or 3-dipentylamine-6-methyl-7-anilinofluorane.

The colour formers can be used as individual substances or as any mixtures of two or more colour formers, provided that the desirable application properties of the recording materials according to the invention are not compromised.

The colour former is preferably present in an amount of from approximately 5 to approximately 30% by weight, especially preferably in an amount of from approximately 8 to approximately 20% by weight, in relation to the total solids content of the heat-sensitive layer.

In order to control specific application properties, it can be advantageous if at least two of the compounds falling under formula (I) are present as colour developer in the heat-sensitive layer.

Likewise, one or more further (bis) phenolic or non-phenolic colour developers can be present in the heat-sensitive colour-forming layer in addition to the compounds of formula (I).

The sensitisation agent is preferably present in an amount of from approximately 10 to approximately 40% by weight, especially preferably in an amount of from approximately 15 to approximately 25% by weight, in relation to the total solids content of the heat-sensitive layer.

In a further preferred embodiment, not only are the colour former, the phenol-free colour developer and the sensitisation agent present in the heat-sensitive colour-forming layer, but optionally also at least one stabiliser (ageing inhibitor).

The stabiliser is preferably constituted by sterically hindered phenols, especially preferably by 1,1,3-tris-(2-methyl-4-hydroxy-5-cyclohexyl-phenyl)butane, 1,1,3-tris-(2-methyl-4-hydroxy-5-tert-butylphenyl)butane, 1,1-bis-(2-methyl-4-hydroxy-5-tert-butyl-phenyl)butane.

Urea-urethane compounds of general formula (II) (commercial product UU) or 4,4'-dihydroxydiphenylsulfone-derived ethers, such as 4-benzyloxy-4'-(2-methylglycidyloxy)-diphenylsulfone (trade name NTZ-95®, Nippon Soda Co. Ltd.), or oligomeric ethers of general formula (III) (trade name D90®, Nippon Soda Co. Ltd.) are also usable as stabilisers in the recording material according to the invention.

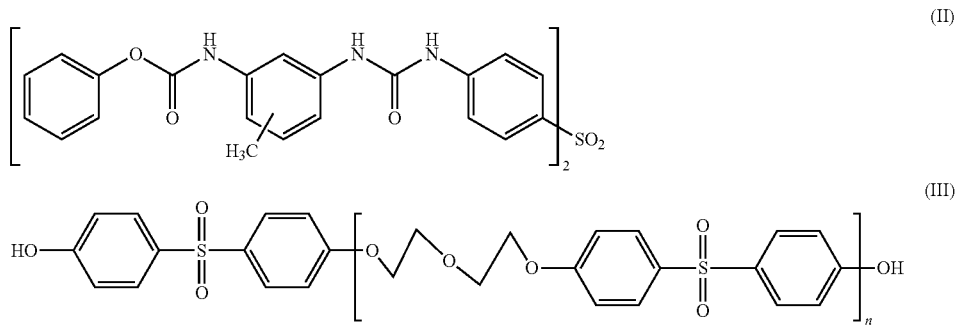

The urea urethane compounds of general formula (II) are especially preferred.

The stabiliser is preferably present in an amount of from 0.2 to 0.5 parts by weight, in relation to 1 part by weight of the at least one phenol-free colour developer of the compound of formula (I).

In a further preferred embodiment at least one binder is present in the heat-sensitive colour-forming layer. This binder is preferably constituted by water-soluble starches, starch derivatives, starch-based biolatices of the Eco-Sphere® type, methyl cellulose, hydroxyethyl cellulose, carboxymethyl cellulose, partially or fully saponified polyvinyl alcohols, chemically modified polyvinyl alcohols or styrene-maleic acid anhydride copolymers, styrene-butadiene copolymers, acrylamide-(meth)acrylate copolymers, acrylamide-acrylate-methacrylate terpolymers, polyacrylates, poly(meth)acrylic esters, acrylate-butadiene copolymers, polyvinyl acetates and/or acrylonitrile-butadiene copolymers.

Besides the at least one colour former and the at least one colour developer, one or more sensitisation agents, also referred to as thermal solvents, can be present in the heat-sensitive colour-forming layer, which has the advantage that the thermal print sensitivity can be controlled more easily.

Crystalline substances of which the melting point is between approximately 90 and approximately 150° C. and which in the molten state dissolve the colour-forming components (colour former and colour developer) without interfering with the formation of the colour complex are generally considered to be advantageous sensitisation agents.

The sensitisation agent is preferably a fatty acid amide, such as stearamide, behenamide or palmitamide, an ethylene-bis-fatty acid amide, such as N,N'-ethylene-bis-stearic acid amide or N,N'-ethylene-bis-oleic acid amide, a fatty acid alkanolamide, such as N-(hydroxymethyl)stearamide, N-hydroxymethylpalmitamide or hydroxyethylstearamide, a wax, such as polyethylene wax or montan wax, a carboxylic acid ester, such as dimethyl terephthalate, dibenzyl terephthalate, benzyl-4-benzyloxy benzoate, di-(4-methylbenzyl) oxalate, di-(4-chlorobenzyl)oxalate or di-(4-benzyl)oxalate, an aromatic ether, such as 1,2-diphenoxyethane, 1,2-di-(3-methylphenoxy)ethane, 2-benzyloxynaphthalene, or 1,4-diethoxynaphthalene, an aromatic sulfone, such as diphenylsulfone, and/or an aromatic sulfonamide, such as benzene sulfonanilide or N-benzyl-4-toluolenesulfonamide or aromatic hydrocarbons, such as 4-benzylbiphenyl.

In a further preferred embodiment at least one separating agent (release agent) or slip additive is present in the heat-sensitive colour-forming layer. These agents are preferably fatty acid metal salts, such as zinc stearate or calcium stearate, or also behenate salts, synthetic waxes, for example in the form of fatty acid amides, such as stearic acid amide and behenic acid amide, fatty acid alkanolamides, such as stearic acid methylolamide, paraffin waxes having different melting points, ester waxes of different molecular weights, ethylene waxes, propylene waxes of different hardnesses and/or natural waxes, such as carnauba wax or montan wax.

The separating agent is preferably present in an amount of from approximately 1 to approximately 10% by weight, especially preferably in an amount of from approximately 3 to approximately 6% by weight, in relation to the total solids content of the heat-sensitive layer.

In a further preferred embodiment the heat-sensitive colour-forming layer contains pigments. The use of these has the advantage, inter alia, that they can fix the chemical melt created in the thermal printing process on their surface. The surface whiteness and opacity of the heat-sensitive colour-forming layer and printability thereof with conventional printing inks can also be controlled via pigments. Lastly, pigments have an "extender function", for example for the relatively costly colour-giving functional chemicals.

Especially suitable pigments are inorganic pigments, both of synthetic and natural origin, preferably clays, precipitated or natural calcium carbonates, aluminium oxides, aluminium hydroxides, silicas, precipitated and pyrogenic silicas (for example Aerodisp® types), diatomaceous earths, magnesium carbonates, talc, but also organic pigments, such as hollow pigments with a styrene/acrylate copolymer wall or urea/formaldehyde condensation polymers. These can be used alone or in any mixtures.

The pigments are preferably present in an amount of from approximately 20 to approximately 50% by weight, especially preferably in an amount of from approximately 30 to approximately 40% by weight, in relation to the total solids content of the heat-sensitive layer.

In order to control the surface whiteness of the heat-sensitive recording material according to the invention, optical brighteners can be incorporated into the heat-sensitive colour-forming layer. These are preferably stilbenes.

In order to improve certain coating properties, it is preferred in individual cases to add further constituents, especially rheology aids, such as thickeners and/or surfactants, to the stated constituents of the heat-sensitive recording material according to the invention.

The areal application weight of the (dry) heat-sensitive layer is preferably approximately 1 to approximately 10 g/m², preferably approximately 3 to approximately 6 g/m².

In an especially preferred embodiment the heat-sensitive recording material is one according to claim 9, wherein a dye of the fluorane type is used as colour former, and a sensitisation means, selected from the group comprising fatty acid amides, aromatic sulfones and/or aromatic ethers, is additionally present. In this preferred embodiment it is also advantageous that approximately 1.5 to approximately 4 parts by weight of the phenol-free colour developer according to claim 1 are present, in relation to 1 part by weight of the colour former.

The preferred embodiments described in conjunction with the compound of formula (I) are also applicable for the heat-sensitive recording material according to the invention.

The heat-sensitive recording material according to the invention can be obtained by means of known production methods.

However, it is preferred to obtain the recording material according to the invention by means of a method in which an aqueous suspension containing the starting materials of the heat-sensitive colour-forming layer is applied to a carrier substrate and dried, wherein the aqueous suspension to be applied has a solids content of from approximately 20 to approximately 75% by weight, preferably from approximately 30 to approximately 50% by weight, and is applied using the curtain-coating process at an operating speed of the coating facility of at least approximately 400 m/min and is dried.

This method is advantageous especially from economical aspects.

If the value of the solids content of approximately 20% by weight is undershot, the cost-efficiency suffers, since a large amount of water has to be removed within a short space of time from the coat by gentle drying, which has a disadvantageous effect on the coating speed. If, on the other hand, the value of 75% by weight is exceeded, this leads merely to an increased technical effort in order to ensure the stability of the coating colour curtain during the coating process.

In the curtain-coating process a free-falling curtain of a coating dispersion is formed. By freefall, the coating dispersion present in the form of a thin film (curtain) is "poured" onto a substrate so as to apply the coating dispersion to the substrate. DE 10196052 T1 discloses the use of the curtain-coating process in the production of information-recording materials, inter alia also of heat-sensitive recording materials, wherein multi-layer recording layers are produced by applying the curtain, comprising a plurality of coating dispersion films, to substrates (maximum speed 200 m/min).

The setting of the operating speed of the coating facility to at least 400 m/min has both economic and technical advantages. The operating speed is preferably at least approximately 750 m/min, especially preferably at least approximately 1000 m/min, and very especially preferably at least approximately 1500 m/min. It was surprising especially that even at the last-mentioned speed the obtained heat-sensitive recording material is not in any way compromised, and operation is optimal even at these high speeds.

In a preferred embodiment of the method according to the invention the aqueous deaerated suspension to be applied has a viscosity of from approximately 150 to approximately 800 mPas (Brookfield, 100 rpms, 20° C.). If the value of approximately 150 mPas is undershot or the value of approximately 800 mPas is exceeded, this leads to defective handling of the coating compound at the coating apparatus. The viscosity of the aqueous deaerated suspension to be applied is especially preferably approximately 200 to approximately 500 mPas.

In a preferred embodiment, in order to optimise the method, the surface tension of the aqueous suspension to be applied can be set to approximately 25 to approximately 60 mN/m, preferably to approximately 35 to approximately 50 mN/m (measured in accordance with the static ring method according to Du Noüy, DIN 53914).

The heat-sensitive colour-forming layer can be formed online or in a separate coating process offline. This is also true for any subsequently applied layers or intermediate layers.

It is advantageous if the dried neat-sensitive colour-forming layer is subjected to a smoothing measure. Here, it is advantageous if the Bekk smoothness, measured in accordance with ISO 5627:1995-03, is set to approximately 100 to approximately 1000 sec., preferably to approximately 250 to approximately 600 sec.

The surface roughness (PPS) according to ISO 8791-4: 2008-05 lies preferably in the range of from approximately 0.50 to approximately 2.50 µm, especially preferably in the range of from 1.00 to 2.00 µm.

The preferred embodiments described in conjunction with the compound of formula (I) are also applicable for the method according to the invention for producing the heat-sensitive recording material according to the invention.

The present invention also relates to a heat-sensitive recording material which is obtainable by the above-described method.

The above-described method is advantageous from economical aspects and allows the method to be performed quickly in the coating facility, even at a speed of more than 1500 m/min, without detriment to the method product, that is to say without detriment to the heat-sensitive recording material according to the invention. The method can be performed online and offline, which results in a desirable flexibility.

The heat-sensitive recording material according to the invention is preferably phenol-free and well suited for POS (point-of-sale), labelling and/or ticketing applications. It is also suitable for the production of parking tickets, travel tickets, entry cards, and lottery and betting slips, etc., which can be printed in direct thermal printing and require a high resistance of the images recorded thereon in the event that the printed text is brought into contact with hydrophobic substances, such as plasticisers, adhesives, greasy or oily substances, etc.

It has surprisingly been found that it is possible to obtain, with the colour developers of formula (I) according to the invention, heat-sensitive recording materials which are characterised by excellent resistance of the printed text to hydrophobic agents and with which a good quality of the printed image (high optical density of the printed image) can be achieved.

Non-phenolic colour developers from the prior art were used as comparison developers, specifically a sulfonyl urea (Pergafast 201® (PF201), BASF) and a urea derivative Z (N-(2-(3-phenylureido)phenyl)benzenesulfonamide).

The invention will be explained in detail hereinafter on the basis of non-limiting examples.

EXAMPLES

Production of the compounds of formula (I) according to the invention.

The compounds I-XXIV (Table 2) were produced as follows:

Step A1—Preparation of the Sulfonamides

A solution of 10 mmol of the corresponding sulfonyl chloride in 75 mL dichloromethane was added dropwise to a solution of 20 mmol aromatic diamine and 20 mmol pyridine in 125 mL dichloromethane at 0° C. under stirring. The reaction solution was stirred for 16 hours at room temperature, before 100 mL water were added. The organic phase was separated and mixed with 250 mL of a 5% aqueous sodium hydroxide solution. The aqueous phase was washed with 100 mL dichloromethane and made neutral by adding 25% hydrochloric acid. After multiple extractions with 100 mL dichloromethane, the combined organic phases were washed with 200 mL water and dried over magnesium sulfate. Following removal of the solvent in a vacuum the sulfonamide remained as a solid. The sulfonamides were used in steps B or C without further purification.

A simple filtration following addition of water to the reaction solution was sufficient to recover the precursor compounds of products IX and XII.

Step A2—Preparation of the Sulfonamides

A solution of 80 mmol of the corresponding sulfonyl chloride in 150 mL dichloroethane was added dropwise to a solution of 80 mmol aromatic amine and 240 mmol potassium carbonate in 500 mL dichloroethane at room temperature under stirring. The reaction mixture was refluxed for six hours, and then 300 mL ethyl acetate and 300 mL water were added. The aqueous phase was made acidic by adding 25% hydrochloric acid. The phases were separated. After multiple extractions of the aqueous phase with 200 mL ethyl acetate, the combined organic phases were washed with 200 mL water and dried over magnesium sulfate. Following removal of the solvent in a vacuum the sulfonamide remained as a solid. The sulfonamides were used in step 3 without further purification.

Step A3-Preparation of the Sulfonamides

A solution of 25.0 mmol of aromatic amine in 35 mL abs. THF was added dropwise to a solution of 27.5 mmol sodium hydride (60% in oil) in 25 mL abs. THF at 0° C. under stirring and protective gas atmosphere. After stirring for two hours at room temperature, a solution of 25.0 mmol of the corresponding sulfonyl chloride in 10 mL abs. THF was added dropwise at 0° C. under stirring. The reaction solution was stirred for 40 hours at room temperature, and then 100 mL water and 100 mL dichloromethane were added. The aqueous phase was made alkaline by adding 5% aqueous sodium hydroxide solution. The phases were separated. The aqueous phase was washed with 100 mL dichloromethane and was made neutral by adding 25% hydrochloric acid. After multiple extractions with 100 mL dichloromethane, the combined organic phases were washed with 200 mL water and dried over magnesium sulfate. Following removal of the solvent in a vacuum the sulfonamide remained as a solid. The sulfonamides were used in step B without further purification.

Step B—Reduction of the Nitro Group to Give the Primary Amine 28.0 mmol (products from step A1) or 56.0 mmol (products from steps A2/A3) $SnCl_2.2H_2O$ were added to a solution of 8.0 mmol of the product from step A1/A2/A3 in 140 mL ethyl acetate at room temperature under stirring. The reaction solution was refluxed. The course of the reaction was monitored by means of thin-film chromatography (eluents: cyclohexane/ethyl acetate 1:1). Once the reaction was complete (approximately 2-3 h), the mixture was diluted with 70 mL ethyl acetate, a 10% aqueous potassium carbonate solution was added, and the mixture was stirred for 30 min at room temperature. The Sn compounds were filtered off and in the filtrate the aqueous phase was separated from the organic phase. The organic phase was washed with 100 ml (2×) of a saturated aqueous sodium chloride solution and dried over magnesium sulfate. Following removal of the solvent in a vacuum, purification was performed by recrystallisation from dichloromethane and a few drops of n-hexane.

Step C1—Preparation of the Sulfonyl Urea Compounds

A solution of 7.0 mmol of the corresponding sulfonyl isocyanate in 10 mL dichloromethane was added dropwise to a solution of 7.0 mmol of the product from step A1 in dichloromethane (20-40 mL) (additionally in 10 mL acetonitrile in the case of poor solubility) at room temperature under stirring. The reaction was monitored by means of thin-film chromatography (eluents: cyclohexane/ethyl acetate 1:1). Once the reaction was complete, the precipitated product was filtered off, washed with dichloromethane, and dried in a vacuum. In some cases the reaction solution was concentrated in the vacuum and the crystallisation was initiated by adding a few drops of n-hexane.

Step C2—Preparation of the Sulfonyl Urea Compounds

A solution of 8.4 mmol of the corresponding sulfonyl isocyanate in DMF (5 to 10 mL) was added dropwise to a solution of 4.2 mmol of the product from step B in DMF (16 mL) under stirring. The reaction was monitored by means of thin-film chromatography (eluents: cyclohexane/ethyl acetate 1:1). Once the reaction was complete, the reaction solution was diluted with 100 mL ethyl acetate and washed with 100 mL (2×) of a saturated aqueous sodium chloride solution and lastly washed with 100 mL water. Following removal of the solvent in a vacuum, purification was performed by recrystallisation from dichloromethane and a few drops of n-hexane.

The compounds I to XIX (Table 2) were prepared starting from the corresponding phenylene diamines in accordance with the general provisions of steps A1 and C1.

The compound XX (Table 2) was produced starting from 2,6-dinitroaniline, which was firstly converted into 1,2-diamino-3-nitrobenzene (reaction scheme 3, V. Milata, J. Saloň, Org. Prep. Proceed. Int., 31 (3), 347 (1999)) and finally was converted into the end product in accordance with the general provisions of steps A1, B and C2.

The compounds XXI to XXIV (Table 2) were prepared starting from 2,4-dinitroaniline (XXI and XXII), 4-nitro-1,2-phenylenediamine (XXIII), and 2,6-dinitroaniline (XXIV) in accordance with the general provisions of steps A1 (XXIII), A2 (XXI and XXII), A3 (XXIV), B (XXI-XXIV) and C2 (XXI-XXIV).

The starting compounds are commercially available.

TABLE 2

Compilation of selected compounds of formula (I)

| | Y | Ar$^1$ | Ar$^2$ | m | n |
|---|---|---|---|---|---|
| I | 1,2-phenylene | C$_6$H$_5$ | C$_6$H$_5$ | 1 | 1 |
| II | 1,2-phenylene | C$_6$H$_5$ | 4-CH$_3$—C$_6$H$_4$ | 1 | 1 |
| III | 1,2-phenylene | 4-CH$_3$—C$_6$H$_4$ | C$_6$H$_5$ | 1 | 1 |
| IV | 1,2-phenylene | 4-CH$_3$—C$_6$H$_4$ | 4-CH$_3$—C$_6$H$_4$ | 1 | 1 |
| V | 1,2-phenylene | 4-(tert-C$_4$H$_9$)—C$_6$H$_4$ | 4-CH$_3$—C$_6$H$_4$ | 1 | 1 |
| VI | 1,2-phenylene | 2,4,6-TriCH$_3$—C$_6$H$_4$ | 4-CH$_3$—C$_6$H$_4$ | 1 | 1 |
| VII | 1,2-phenylene | 4-OCH$_3$—C$_6$H$_4$ | 4-CH$_3$—C$_6$H$_4$ | 1 | 1 |
| VIII | 1,2-phenylene | 4-Cl—C$_6$H$_4$ | 4-CH$_3$—C$_6$H$_4$ | 1 | 1 |
| IX | 1,2-phenylene | 4-(NH—CO—CH$_3$)—C$_6$H$_4$ | 4-CH$_3$—C$_6$H$_4$ | 1 | 1 |
| X | 1,2-phenylene | 4-NO$_2$—C$_6$H$_4$ | 4-CH$_3$—C$_6$H$_4$ | 1 | 1 |
| XI | 1,2-phenylene | 2-(CO$_2$CH$_3$)—C$_6$H$_4$ | 4-CH$_3$—C$_6$H$_4$ | 1 | 1 |
| XII | 1,2-phenylene | 2-naph | 4-CH$_3$—C$_6$H$_4$ | 1 | 1 |
| XIII | 1,2-phenylene | C$_6$H$_5$—CH$_2$ | 4-CH$_3$—C$_6$H$_4$ | 1 | 1 |
| XIV | 1,3-phenylene* | C$_6$H$_5$ | 4-CH$_3$—C$_6$H$_4$ | 1 | 1 |
| XV | 1,3-phenylene* | 4-CH$_3$—C$_6$H$_4$ | C$_6$H$_5$ | 1 | 1 |
| XVI | 1,3-phenylene* | 4-CH$_3$—C$_6$H$_4$ | 4-CH$_3$—C$_6$H$_4$ | 1 | 1 |
| XVII | 1,4-phenylene* | C$_6$H$_5$ | 4-CH$_3$—C$_6$H$_4$ | 1 | 1 |
| XVIII | 1,4-phenylene* | 4-CH$_3$—C$_6$H$_4$ | C$_6$H$_5$ | 1 | 1 |
| XIX | 1,4-phenylene* | 4-CH$_3$—C$_6$H$_4$ | 4-CH$_3$—C$_6$H$_4$ | 1 | 1 |
| XX | benzene-1,2,3-triyl | 4-CH$_3$—C$_6$H$_4$ | 4-CH$_3$—C$_6$H$_4$ | 1 | 2 |
| XXI | benzene-1,2,4-triyl | 4-CH$_3$—C$_6$H$_4$ | C$_6$H$_5$ | 1 | 2 |
| XXII | benzene-1,2,4-triyl | 4-CH$_3$—C$_6$H$_4$ | 4-CH$_3$—C$_6$H$_4$ | 1 | 2 |
| XXIII | benzene-1,2,5-triyl | 4-CH$_3$—C$_6$H$_4$ | 4-CH$_3$—C$_6$H$_4$ | 1 | 2 |
| XXIV | benzene-1,2,6-triyl | 4-CH$_3$—C$_6$H$_4$ | 4-CH$_3$—C$_6$H$_4$ | 1 | 2 |

*comparative examples

Analytical Data:

I, C$_{19}$H$_{17}$N$_3$O$_5$S$_2$, M=431.5, N-((2-(phenylsulfonamido)phenyl)carbamoyl)benzenesulfonamide MS (ESI): m/z (%)=430.0 (14) [M–H]$^-$, 273.0 (100) [M–H–Ar$^2$SO$_2$NH$_2$]$^-$, 247.0 (15) [M–H–Ar$^2$SO$_2$NCO]$^-$.

*H-NMR (500 MHz, DMSO-d$_6$): δ (ppm)=11.66 (1H, s), 9.60 (1H, s), 8.57 (1H, s), 8.01-7.99 (2H, m), 7.86 (1H, dd, J=8.3, 1.3 Hz), 7.73-7.69 (1H, m), 7.68-7.62 (5H, m), 7.56-7.53 (2H, m), 7.16-7.12 (1H, m), 6.80 (1H, ddd, J=8.9, 7.9, 1.4 Hz), 6.39 (1H, dd, J=7.9, 1.1 Hz).

$^{13}$C-NMR (126 MHz, DMSO-d$_6$): δ (ppm)=149.12 (NHCONH), 39.78, 138.87, 135.56, 133.39, 133.01, 129.10, 129.03, 127.82, 127.27, 127.23, 127.08, 125.28, 123.15, 120.75.

II, C$_{20}$H$_{19}$N$_3$O$_5$S$_2$, M=445.5, N-((2-(phenylsulfonamido)phenyl)carbamoyl)tosylamide MS (ESI): m/z (%)=444.0 (23) [M–H]$^-$, 273.0 (100) [M–H–Ar$^2$SO$_2$NH$_2$]$^-$, 247.1 (21) [M–H–Ar$^2$SO$_2$NCO]$^-$.

$^1$H-NMR (500 MHz, DMSO-d$_6$): δ (ppm)=11.58 (1H, s), 9.60 (1H, s), 8.56 (1H, s), 7.89-7.86 (3H, m), 7.68-7.66 (2H, m), 7.65-7.62 (1H, m), 7.56-7.53 (2H, m), 7.44-7.43 (2H, m), 7.16-7.12 (1H, m), 6.79 (1H, ddd, J=8.9, 7.7, 1.4 Hz), 6.38 (1H, dd, J=7.9, 1.3 Hz), 2.39 (3H, s).

$^{13}$C-NMR (126 MHz, DMSO-d$_6$): δ (ppm)=149.16 (NHCONH), 143.93, 138.90, 136.95, 135.67, 133.02, 129.52, 129.05, 127.84, 127.37, 127.25, 127.10, 125.22, 123.08, 120.68, 21.00 (CH$_3$).

III, C$_{20}$H$_{19}$N$_3$O$_5$S$_2$, M=445.5, N-(2-(3-(phenylsulfonyl)ureido)phenyl)tosylamide MS (ESI): m/z (%)=444.0 (17) [M–H]$^-$, 287.0 (100) [M–H–Ar$^2$SO$_2$NH$_2$]$^-$, 261.1 (7) [M–H–Ar$^2$SO$_2$NCO]$^-$.

$^1$H-NMR (500 MHz, DMSO-d$_6$): δ (ppm)=11.66 (1H, s), 9.51 (1H, s), 8.56 (1H, s), 8.01-7.99 (2H, m), 7.85 (1H, dd, J=8.3, 1.4 Hz), 7.73-7.69 (1H, m), 7.66-7.63 (2H, m), 7.56-7.54 (2H, m), 7.35-7.33 (2H, m), 7.15-7.11 (1H, m), 6.81 (1H, ddd, 9.1, 7.7, 1.4 Hz), 6.43-6.42 (1H, m), 2.36 (3H, s).

$^{13}$C-NMR (126 MHz, DMSO-d$_6$): δ (ppm)=149.13 (NHCONH), 143.34, 139.80, 136.07, 135.48, 133.38, 129.47, 129.09, 127.70, 127.26, 127.18, 127.13, 125.43, 123.16, 120.73, 20.96 (CH$_3$).

IV, C$_{21}$H$_{21}$N$_3$O$_5$S$_2$, M=459.5, N-((2-(tosylamido)phenyl)carbamoyl)tosylamide MS (ESI): m/z (%)=458.1 (26) [M–H]$^-$, 287.0 (100) [M–H–Ar$^2$SO$_2$NH$_2$]$^-$, 261.0 (10) [M–H–Ar$^2$SO$_2$NCO]$^-$.

$^1$H-NMR (500 MHz, DMS0-d$_6$): δ (ppm)=11.58 (1H, s), 9.50 (1H, s), 8.55 (1H, s), 7.89-7.85 (3H, m), 7.56-7.54 (2H, m), 7.44-7.42 (2H, m), 7.35-7.33 (2H, m), 7.15-7.11 (1H, m), 6.80 (1H, ddd, J=9.0, 7.7, 1.4 Hz), 6.43-6.41 (1H, m), 2.39 (3H, s), 2.36 (3H, s).

$^{13}$C-NMR (126 MHz, DMSO-d$_6$): δ (ppm)=149.15 (NHCONH), 143.88, 143.33, 136.98, 136.11, 135.59, 129.49, 129.45, 127.70, 127.36, 127.19, 127.15, 125.37, 123.07, 120.65, 20.98 (CH$_3$), 20.94 (CH$_3$).

V, C$_{24}$H$_{27}$N$_3$O$_5$S$_2$, M=501.6, N-(2-(3-tosylureido)phenyl)-4-tert-butylbenzenesulfonamide MS (ESI): m/z (%)=500.1 (56) [M–H]$^-$, 329.1 (100) [M–H–Ar$^2$SO$_2$NH$_2$]$^-$.

$^1$H-NMR (500 MHz, DMSO-d$_6$): δ (ppm)=11.57 (1H, s), 9.53 (1H, s), 8.55 (1H, s), 7.89-7.87 (2H, m), 7.86-7.85 (1H, m), 7.62-7.60 (2H, m), 7.58-7.56 (2H, m), 7.44-7.42 (2H, m), 7.14-7.11 (1H, m), 6.80-6.77 (1H, m), 6.42-6.40 (1H, m), 2.39 (3H, s), 1.28 (9H, s).

$^{13}$C-NMR (126 MHz, DMSO-d$_6$): δ (ppm)=156.10, 149.16 (NHCONH), 143.89, 136.96, 136.15, 135.48, 129.51, 127.66, 127.35, 127.03, 127.03, 125.84, 125.44, 123.05, 120.68, 34.83 (C(CH$_3$)$_3$), 30.71 (C(CH$_3$)$_3$), 21.00 (CH$_3$).

VI, $C_{23}H_{25}N_3O_5S_2$, M=487.6, N-(2-(3-tosylureido)phenyl)-2,4,6-trimethylbenzenesulfonamide MS (ESI): m/z (%)=486.1 (37) $[M-H]^-$, 315.1 (100) $[M-H-Ar^2SO_2NH_2]^-$, 289.1 (18) $[M-H-Ar^2SO_2NCO]^-$.

$^1$H-NMR (500 MHz, DMSO-$d_6$): δ (ppm)=11.66 (1H, s), 9.26 (1H, s), 8.62 (1H, s), 7.89-7.87 (3H, m), 7.44-7.42 (2H, m), 7.18-7.14 (1H, m), 6.98 (2H, s), 6.77 (1H, ddd, J=9.0, 7.7, 1.4 Hz), 6.26 (1H, dd, J=7.9, 1.3 Hz), 2.39 (3H, s), 2.29 (6H, s), 2.24 (3H, s).

$^{13}$C-NMR (126 MHz, DMSO-$d_6$): δ (ppm)=149.26 (NH$\underline{C}$ONH), 143.87, 142.02, 138.89, 136.96, 136.06, 133.30, 131.54, 129.48, 127.99, 127.83, 127.35, 124.76, 123.09, 120.55, 22.42 (2x$\underline{C}$H$_3$), 20.98 ($\underline{C}$H$_3$), 20.36 ($\underline{C}$H$_3$).

VII, $C_{21}H_{21}N_3O_6S_2$, M=475.5, N-(2-(3-tosylureido)phenyl)-4-methoxybenzenesulfonamide MS (ESI): m/z (%)=474.1 (28) $[M-H]^-$, 303.0 (100) $[M-H-Ar^2SO_2NH_2]^-$.

$^1$H-NMR (500 MHz, DMSO-$d_6$): δ (ppm)=11.59 (1H, s), 9.42 (1H, s), 8.56 (1H, s), 7.89-7.85 (3H, m), 7.60-7.58 (2H, m), 7.44-7.42 (2H, m), 7.15-7.12 (1H, m), 7.07-7.05 (2H, m), 6.82 (1H, ddd, J=8.7, 7.7, 1.0 Hz), 6.43 (1H, dd, J=7.9, 1.1 Hz), 3.82 (3H, s), 2.39 (3H, s).

$^{13}$C-NMR (126 MHz, DMSO-$d_6$): δ (ppm)=162.53, 149.16 (NH$\underline{C}$ONH), 143.90, 136.96, 135.64, 130.47, 129.50, 129.34, 127.70, 127.34, 127.30, 125.46, 123.07, 120.58, 114.17, 55.60 (O$\underline{C}$H$_3$), 20.99 ($\underline{C}$H$_3$).

VIII, $C_{20}H_{18}ClN_3O_5S_2$, M=480.0, N-(2-(3-tosylureido)phenyl)-4-chlorobenzenesulfonamide MS (ESI): m/z (%)=478.0 (29) $[M-H]^-$, 307.0 (100) $[M-H-Ar^2SO_2NH_2]^-$, 281.0 (49) $[M-H-Ar^2SO_2NCO]^-$.

$^1$H-NMR (500 MHz, DMSO-$d_6$): δ (ppm)=11.56 (1H, s), 9.70 (1H, s), 8.55 (1H, s), 7.88-7.86 (3H, m), 7.67-7.65 (2H, m), 7.63-7.61 (2H, m), 7.44-7.43 (2H, m), 7.18-7.14 (1H, m), 6.84 (1H, ddd, J=9.2, 7.9, 1.4 Hz), 6.44 (1H, dd, J=7.9, 1.5 Hz), 2.39 (3H, s).

$^{13}$C-NMR (126 MHz, DMSO-$d_6$): δ (ppm)=149.13 (NH$\underline{C}$ONH), 143.93, 137.95, 137.77, 136.91, 135.65, 129.52, 129.24, 129.04, 128.00, 127.35, 127.28, 124.97, 123.26, 120.79, 21.00 ($\underline{C}$H$_3$).

IX, $C_{22}H_{22}N_4O_6S_2$, M=502.6, N-(4-(N-(2-(3-tosylureido)phenyl)sulfamoyl)phenyl) acetamide MS (ESI): m/z (%)=501.0 (32) $[M-H]^-$, 330.1 (100) $[M-H-Ar^2SO_2NH_2]^-$.

$^1$H-NMR (500 MHz, DMSO-$d_6$): δ (ppm)=11.60 (1H, s), 10.30 (1H, s), 9.45 (1H, s), 8.56 (1H, s), 7.89-7.86 (3H, m), 7.75-7.73 (2H, m), 7.60-7.57 (2H, m), 7.44-7.42 (2H, m), 7.15-7.12 (1H, m), 6.81 (1H, ddd, J=9.0, 7.6, 1.4 Hz), 6.40 (1H, dd, J=7.9, 1.4 Hz), 2.39 (3H, s), 2.09 (3H, s).

$^{13}$C-NMR (126 MHz, DMSO-$d_6$): δ (ppm)=169.01 (NH$\underline{C}$OCH$_3$), 149.19 (NH$\underline{C}$ONH), 143.91, 143.26, 136.96, 135.69, 132.36, 129.51, 128.38, 127.73, 127.35, 127.28, 125.41, 123.08, 120.59, 118.34, 24.11 ($\underline{C}$H$_3$), 21.00 ($\underline{C}$H$_3$).

X, $C_{20}H_{18}N_4O_7S_2$, M=490.5, N-((2-(4-nitrophenylsulfonamido)phenyl)carbamoyl)tosylamide MS (ESI): m/z (%)=489.0 (31) $[M-H]^-$, 318.0 (55) $[M-H-Ar^2SO_2NH_2]^-$, 292.0 (100) $[M-H-Ar^2SO_2NCO]^-$.

$^1$H-NMR (500 MHz, DMSO-$d_6$): δ (ppm)=11.51 (1H, s), 9.97 (1H, s), 8.52 (1H, s), 8.40-8.37 (2H, m), 7.92-7.89 (2H, m), 7.87-7.84 (3H, m), 7.44-7.42 (2H, m), 7.20-7.16 (1H, m), 6.85 (1H, ddd, J=8.9, 7.7, 1.4 Hz), 6.48 (1H, dd, J=7.9, 1.3 Hz), 2.39 (3H,s).

$^{13}$C-NMR (126 MHz, DMSO-$d_6$): δ (ppm)=149.88, 149.13 (NH$\underline{C}$ONH), 144.49, 143.96, 136.89, 135.60, 129.52, 128.67, 128.24, 127.50, 127.33, 124.71, 124.47, 123.50, 121.08, 21.00 ($\underline{C}$H$_3$).

XI, $C_{22}H_{21}N_3O_7S_2$, M=503.5, methyl 2-(N-(2-(3-tosylureido)phenyl)sulfamoyl) benzoate MS (ESI): m/z (%)=502.1 (32) $[M-H]^-$, 331.0 (100) $[M-H-Ar^2SO_2NH_2]^-$, 305.0 (31) $[M-H-Ar^2SO_2NCO]^-$.

$^1$H-NMR (500 MHz, DMSO-$d_6$): δ (ppm)=11.53 (1H, s), 9.21 (1H, s), 8.53 (1H, s), 7.88-7.86 (2H, m), 7.82-7.81 (1H, m), 7.73-7.72 (2H, m), 7.67-7.65 (2H, m), 7.44-7.42 (2H, m), 7.18-7.15 (1H, m), 6.85-6.82 (1H, m), 6.55-6.54 (1H, m), 3.72 (3H, s), 2.39 (3H, s).

$^{13}$C-NMR (126 MHz, DMSO-$d_6$): δ (ppm)=167.35 ($\underline{C}$OOCH$_3$), 149.29 (NH$\underline{C}$ONH), 143.90, 136.93, 136.57, 135.40, 133.17, 132.03, 130.94, 129.49, 129.13, 129.11, 127.91, 127.42, 127.34, 125.39, 123.43, 121.21, 52.87 (COO$\underline{C}$H$_3$), 20.98 ($\underline{C}$H$_3$).

XII, $C_{24}H_{21}N_3O_5S_2$, M=495.6, N-(2-(3-tosylureido)phenyl)naphthalene-2-sulfonamide MS (ESI): m/z (%)=494.1 (24) $[M-H]^-$, 323.0 (100) $[M-H-Ar^2SO_2NH_2]^-$, 297.0 (26) $[M-H-Ar^2SO_2NCO]^-$.

$^1$H-NMR (500 MHz, DMSO-$d_6$): δ (ppm)=11.64 (1H, s), 9.73 (1H, s), 8.64 (1H, s), 8.27 (1H, d, J=1.4 Hz), 8.13-8.12 (1H, m), 8.08-8.06 (1H, m), 8.04-8.02 (1H, m), 7.90-7.89 (2H, m), 7.89 (1H, dd, J=8.3, 1.3 Hz), 7.80 (1H, dd, J=8.7, 1.9 Hz), 7.71-7.68 (1H, m), 7.65-7.61 (1H, m), 7.45-7.43 (2H, m), 7.12-7.09 (1H, m), 6.71-6.68 (1H, m), 6.37-6.36 (1H, m), 2.39 (3H, s).

$^{13}$C-NMR (126 MHz, DMSO-$d_6$): δ (ppm)=149.19 (NH$\underline{C}$ONH), 143.92, 136.96, 135.95, 135.74, 134.29, 131.43, 129.52, 129.26, 129.19, 128.94, 128.34, 127.84, 127.81, 127.61, 127.37, 127.22, 125.21, 123.09, 122.45, 120.67, 20.99 ($\underline{C}$H$_3$).

XIII, $C_{21}H_{21}N_3O_5S_2$, M=459.5, N-((2-(benzylsulfonamido)phenyl)carbamoyl)tosylamide MS (ESI): m/z (%)=458.0 (16) $[M-H]^-$, 287.0 (100) $[M-H-Ar^2SO_2NH_2]^-$, 261.1 (13) $[M-H-Ar^2SO_2NCO]^-$.

$^1$H-NMR (500 MHz, DMSO-$d_6$): δ (ppm)=11.47 (1H, s), 9.25 (1H, s), 8.40 (1H, s), 7.86-7.84 (2H, m), 7.81 (1H, dd, J=8.4, 1.4 Hz), 7.39-7.34 (8H, m), 7.25-7.21 (1H, m), 7.10 (1H, ddd, J=9.0, 7.6, 1.5 Hz), 4.40 (2H, s), 2.36 (3H, s).

$^{13}$C-NMR (126 MHz, DMSO-$d_6$): δ (ppm)=149.33 (NH$\underline{C}$ONH), 143.87, 136.93, 134.39, 130.83, 129.46, 129.06, 128.33, 128.16, 127.52, 127.33, 127.33, 126.50, 123.97, 121.66, 57.25 ($\underline{C}$H$_2$), 20.98 ($\underline{C}$H$_3$).

XIV, $C_{20}H_{19}N_3O_5S_2$, M=445.5, N-((3-(phenylsulfonamido)phenyl)carbamoyl)tosylamide MS (ESI): m/z (%)=444.0 (100) $[M-H]^-$, 272.9 (7) $[M-H-Ar^2SO_2NH_2]^-$.

$^1$H-NMR (500 MHz, DMSO-$d_6$): δ (ppm)=10.55 (1H, s), 10.24 (1H, s), 8.83 (1H, s), 7.86-7.84 (2H, m), 7.76-7.74 (2H, m), 7.59-7.56 (1H, m), 7.52-7.49 (2H, m), 7.43-7.41 (2H, m), 7.24-7.23 (1H, m), 7.10-7.07 (1H, m), 6.97 (1H, ddd, J=8.2, 2.0, 0.8 Hz), 6.76 (1H, ddd, J=8.1, 2.1, 0.9 Hz), 2.39 (3H, s).

$^{13}$C-NMR (126 MHz, DMSO-d$_6$): δ (ppm)=149.05 (NH<u>C</u>ONH), 143.80, 139.46, 138.70, 138.19, 137.01, 132.$\overline{79}$, 129.39, 129.39, 129.11, 127.45, 126.58, 114.42, 114.34, 110.23, 20.98 (<u>C</u>H$_3$).

XV, C$_{20}$H$_{19}$N$_3$O$_5$S$_2$, M=445.5, N-(3-(3-(phenylsulfonyl)ureido)phenyl)tosylamide MS (ESI): m/z (%)=444.0 (100) [M–H]$^-$, 287.0 (6) [M–H–Ar$^2$SO$_2$NH$_2$]$^-$.
$^1$H-NMR (500 MHz, DMSO-d$_6$): δ (ppm)=10.44 (1H, s), 10.17 (1H, s), 8.87 (1H, s), 7.99-7.97 (2H, m), 7.71-7.68 (1H, m), 7.64-7.61 (4H, m), 7.30-7.28 (2H, m), 7.24-7.23 (1H, m), 7.10-7.07 (1H, m), 6.97 (1H, ddd, J=8.2, 2.1, 0.9 Hz), 6.76 (1H, ddd, J=8.1, 2.1, 0.9 Hz), 2.30 (3H, s).
$^{13}$C-NMR (126 MHz, DMSO-d$_6$): δ (ppm)=149.03 (NH<u>C</u>ONH), 143.16, 139.90, 138.64, 138.34, 136.61, 133.$\overline{28}$, 129.54, 129.36, 128.97, 127.37, 126.66, 114.27, 114.22, 110.04, 20.87 (<u>C</u>H$_3$).

XVI, C$_{21}$H$_{21}$N$_3$O$_5$S$_2$, M=459.5, N-((3-(tosylamido)phenyl)carbamoyl)tosylamide MS (ESI): m/z (%)=458.1 (100) [M–H]$^-$, 287.0 (4) [M–H–Ar$^2$SO$_2$NH$_2$]$^-$.
$^1$H-NMR (500 MHz, DMSO-d$_6$): δ (ppm)=10.53 (1H, s), 10.17 (1H, s), 8.82 (1H, s), 7.86-7.85 (2H, m), 7.65-7.63 (2H, m), 7.42-7.41 (2H, m), 7.30-7.28 (2H, m), 7.24-7.24 (1H, m), 7.10-7.06 (1H, m), 6.97-6.95 (1H, m), 6.77-6.75 (1H, m), 2.38 (3H, s), 2.30 (3H, s).
$^{13}$C-NMR (126 MHz, DMSO-d$_6$): δ (ppm)=149.05 (NH<u>C</u>ONH), 143.80, 143.15, 138.68, 138.35, 137.03, 136.$\overline{62}$, 129.54, 129.39, 129.36, 127.46, 126.67, 114.22, 114.17, 109.98, 20.99 (<u>C</u>H$_3$), 20.87 (<u>C</u>H$_3$).

XVII, C$_{26}$H$_{19}$N$_3$O$_5$S$_2$, M=445.5, N-((4-(phenylsulfonamido)phenyl)carbamoyl)tosylamide MS (ESI): m/z (%)=444.0 (100) [M–H]$^-$, 273.0 (5) [M–H–Ar$^2$SO$_2$NH$_2$]$^-$.
$^1$H-NMR (500 MHz, DMSO-d$_6$): δ (ppm)=10.47 (1H, s), 10.05 (1H, s), 8.70 (1H, s), 7.84-7.62 (2H, m), 7.70-7.68 (2H, m), 7.58-7.55 (1H, m), 7.52-7.49 (2H, m), 7.40-7.39 (2H, m), 7.20-7.18 (2H, m), 6.99-6.97 (2H, m), 2.37 (3H, s).
$^{13}$C-NMR (126 MHz, DMSO-d$_6$): δ (ppm)=149.19 (NH<u>C</u>ONH), 143.77, 139.39, 137.06, 134.61, 132.72, 132.$\overline{72}$, 129.41, 129.09, 127.41, 126.59, 121.63, 119.83, 20.99 (<u>C</u>H$_3$).

XVIII, C$_{20}$H$_{19}$N$_3$O$_5$S$_2$, M=445.5, N-(4-(3-(phenylsulfonyl)ureido)phenyl)tosylamide MS (ESI): m/z (%)=444.0 (100) [M–H]$^-$, 287.0 (5) [M–H–Ar$^2$SO$_2$NH$_2$]$^-$.
$^1$H-NMR (500 MHz, DMSO-d$_6$): δ (ppm)=10.70 (1H, s), 9.98 (1H, s), 8.73 (1H, s), 7.96-7.95 (2H, m), 7.69-7.66 (1H, m), 7.62-7.57 (4H, m), 7.30-7.29 (2H, m), 7.20-7.18 (2H, m), 7.00-6.97 (2H, m), 2.30 (3H, s)
$^{13}$C-NMR (126 MHz, DMSO-d$_6$): δ (ppm)=149.16 (NH<u>C</u>ONH), 143.04, 139.94, 136.56, 134.40, 133.25, 132.$\overline{96}$, 129.51, 128.98, 127.31, 126.64, 121.41, 119.91, 20.87 (<u>C</u>H$_3$).

XIX, C$_{21}$H$_{21}$N$_3$O$_5$S$_2$, M=459.5, N-((4-(tosylamido)phenyl)carbamoyl)tosylamide MS (ESI): m/z (%)=458.1 (100) [M–H]$^-$, 287.1 (4) [M–H–Ar$^2$SO$_2$NH$_2$]$^-$.
$^1$H-NMR (500 MHz, DMSO-d$_6$): δ (ppm)=10.55 (1H, s), 9.97 (1H, s), 8.68 (1H, s), 7.84-7.82 (2H, m), 7.59-7.57 (2H, m), 7.40-7.39 (2H, m), 7.30-7.28 (2H, m), 7.20-7.17 (2H, m), 7.00-6.97 (2H, m), 2.37 (3H, s), 2.30 (3H, s).
$^{13}$C-NMR (126 MHz, DMSO-d$_6$): δ (ppm)=149.17 (NH<u>C</u>ONH), 143.75, 143.03, 137.07, 136.56, 134.44, 132.$\overline{91}$, 129.51, 129.39, 127.39, 126.63, 121.42, 119.84, 20.97 (<u>C</u>H$_3$), 20.86 (<u>C</u>H$_3$).

XX, C$_{29}$H$_{29}$N$_5$O$_8$S$_3$, M=671.8, N,N'-(((3-tosylamido-1,2-phenylene)bis(azandiyl))bis(carbonyl))bis(tosylamide)

MS (ESI): m/z (%)=670.0 (21) [M–H]$^-$, 499.0 (100) [M–H–Ar$^2$SO$_2$NH$_2$]$^-$, 302.0 (70) [M–H–Ar$^2$SO$_2$NCO–Ar$^2$SO$_2$NH$_2$]$^-$.
$^1$H-NMR (500 MHz, DMSO-d$_6$): δ (ppm)=11.38 (1H, s), 11.18 (1H, s), 9.47 (1H, s), 8.16 (1H, s), 7.91 (1H, s), 7.91-7.89 (2H, m), 7.80-7.78 (2H, m), 7.54-7.53 (1H, m), 7.49-7.47 (2H, m), 7.42-7.40 (4H, m), 7.29-7.28 (2H, m), 7.00-6.97 (1H, m), 6.42-6.40 (1H, m), 2.39 (3H, s), 2.38 (3H, s), 2.34 (3H, s).
$^{13}$C-NMR (126 MHz, DMSO-d$_6$): δ (ppm)=150.34 (NH<u>C</u>ONH), 149.01 (NH<u>C</u>ONH), 143.91, 143.64, 143.34, 137.$\overline{20}$, 136.81, 136.01, $\overline{1}$35.71, 133.30, 129.52, 129.50, 129.45, 127.22, 127.20, 126.89, 125.57, 122.98, 119.81, 119.08, 21.01 (<u>C</u>H$_3$), 21.01 (<u>C</u>H$_3$), 20.95 (<u>C</u>H$_3$).

XXI, C$_{27}$H$_{25}$N$_5$O$_8$S$_3$, M=643.7, N,N'-(((4-tosylamido-1,3-phenylene)bis(azandiyl))bis(carbonyl))bis(benzenesulfonamide)

MS (ESI): m/z (%)=644.0 (79) [M–H]$^+$.
$^1$H-NMR (500 MHz, DMSO-d$_6$): δ (ppm)=11.69 (1H, s), 10.62 (1H, s), 9.36 (1H, s), 8.94 (1H, s), 8.53 (1H, s), 8.00-7.98 (2H, m), 7.95-7.93 (2H, m), 7.91 (1H, d, J=2.5 Hz), 7.74-7.59 (6H, m), 7.52-7.50 (2H, m), 7.33-7.32 (2H, m), 6.86 (1H, dd, J=8.7, 2.5 Hz), 6.23 (1H, d, J=8.7 Hz), 2.35 (3H, s).
$^{13}$C-NMR (126 MHz, DMSO-d$_6$): δ (ppm)=145.05 (NH<u>C</u>ONH), 148.98 (NH<u>C</u>ONH), 143.35, 139.85, 139.72, 137.$\overline{58}$, 136.32, 135.91, $\overline{1}$33.45, 133.30, 129.47, 129.13, 129.01, 127.95, 127.35, 127.21, 125.84, 119.89, 113.18, 110.52, 20.98 (<u>C</u>H$_3$).

XXII, C$_{29}$H$_{29}$N$_5$O$_8$S$_3$, M=671.8, N,N'-(((4-tosylamido-1,3-phenylene)bis(azandiyl))bis(carbonyl))bis(tosylamide)

MS (ESI): m/z (%)=670.0 (15) [M–H]$^-$, 499.0 (100) [M–H–Ar$^2$SO$_2$NH$_2$]$^-$, 473.0 (2) [M–H–Ar$^2$SO$_2$NCO]$^-$, 328.0 (5) [M–H–2xAr$^2$SO$_2$NH$_2$]$^-$.
$^1$H-NMR (500 MHz, DMSO-d$_6$): δ (ppm)=11.60 (1H, s), 10.69 (1H, s),9.34 (1H, s), 9.18 (1H, s), 8.55 (1H, s), 7.91 (1H, d, J=2.4 Hz), 7.87-7.85 (2H, m), 7.82-7.80 (2H, m), 7.51-7.50 (2H, m), 7.45-7.43 (2H, m), 7.40-7.39 (2H, m), 7.32-7.31 (2H, m), 6.82 (1H, dd, J=8.7, 2.4 Hz), 6.24 (1H, d, J=8.7 Hz), 2.40 (3H, s), 2.38 (3H, s), 2.35 (3H, s).
$^{13}$C-NMR (126 MHz, DMSO-d$_6$): δ (ppm)=149.09 (NH<u>C</u>ONH), 148.93 (NH<u>C</u>ONH), 143.95, 143.76, 143.31, 137.$\overline{61}$, 136.99, 136.87, $\overline{1}$36.29, 135.91, 129.54, 129.42, 129.42, 127.92, 127.40, 127.38, 127.21, 119.77, 112.96, 110.27, 21.01 (<u>C</u>H$_3$), 21.00 (<u>C</u>H$_3$), 20.99 (<u>C</u>H$_3$).

XXIII, C$_{29}$H$_{29}$N$_5$O$_8$S$_3$, M=671.8, N,N'-(((2-tosylamido-1,4-phenylene)bis(azandiyl))bis(carbonyl))bis(tosylamide)

MS (ESI): m/z (%)=670.0 (60) [M–H]$^-$, 499.0 (100) [M–H–Ar$^2$SO$_2$NH$_2$]$^-$.

$^1$H-NMR (500 MHz, DMSO-d$_6$): δ (ppm)=11.38 (1H, s), 10.47 (1H, s), 9.47 (1H, s), 8.68 (1H, s), 8.33 (1H, s), 7.86-7.84 (2H, m), 7.82-7.81 (2H, m), 7.62 (1H, d, J=9.0 Hz), 7.54-7.52 (2H, m), 7.43-7.41 (4H, m), 7.28-7.26 (2H, m), 7.05 (1H, dd, J=9.0, 2.5 Hz), 6.76 (1H, d, J=2.5 Hz), 2.39 (3H, s), 2.38 (3H, s), 2.32 (3H, s).

$^{13}$C NMR (126 MHz, DMSO-d$_6$): δ (ppm)=149.20 (NHCONH), 148.86 (NHCONH), 143.87, 143.78, 143.32, 137.05, 137.02, 135.99, 133.65, 129.88, 129.51, 129.45, 129.37, 127.43, 127.35, 127.02, 126.39, 121.75, 117.81, 117.28, 21.01 (CH$_3$), 21.01 (CH$_3$), 20.97 (CH$_3$).

XXIV, C$_{29}$H$_{29}$N$_5$O$_8$S$_3$, M=671.8, N,N'-(((2-tosylamido-1,3-phenylene)bis(azandiyl))bis(carbonyl))bis(tosylamide)

MS (ESI): m/z (%)=670.1 (100) [M–H]$^-$, 499.0 (33) [M–H–Ar$^2$SO$_2$NH$_2$]$^-$, 473.0 (29) [M–H–Ar$^2$SO$_2$NCO–Ar$^2$SO$_2$NH$_2$]$^-$, 328.1 (23) [M–H–2xAr$^2$SO$_2$NH$_2$]$^-$, 302.0 (21) [M–H–Ar$^2$SO$_2$NCO–Ar$^2$SO$_2$NH$_2$]$^-$.

$^1$H-NMR (500 MHz, DMSO-d$_6$): δ (ppm)=11.22 (2H, s), 8.91 (1H, s), 8.13 (2H, s), 7.84-7.82 (4H, m), 7.43-7.42 (4H, m), 7.40-7.38 (2H, m), 7.37-7.35 (2H, m), 7.19-7.17 (2H, m), 7.13-7.09 (1H, m), 2.39 (6H, s), 2.27 (3H, s).

$^{13}$C NMR (126 MHz, DMSO-d$_6$): δ (ppm)=148.89 (NHCONH), 143.85, 143.78, 136.95, 136.62, 135.51, 129.44, 129.22, 128.40, 127.28, 126.87, 116.40, 115.44, 20.97 (CH$_3$), 20.95 (CH$_3$), 20.95 (CH$_3$).

An aqueous suspension to be applied for forming the heat-sensitive colour-forming layer of a heat-sensitive recording paper was applied on a laboratory scale by means of a doctor bar to one side of a synthetic base paper (Yupo® FP680) with a grammage of 63 g/m$^2$. Once dry, a thermal recording material sheet was obtained. The applied amount of the heat-sensitive colour-forming layer was between 3.8 and 4.2 g/m$^2$.

A heat-sensitive recording material or thermal paper was produced on the basis of the details provided above, wherein the following formulations of aqueous suspensions to be applied were used to form a composite structure on a carrier substrate, and then the further layers, especially a protective layer, were formed in the usual manner, which will not be detailed separately here.

Preparation of the dispersions (in each case for 1 part by weight) for the suspensions to be applied An aqueous dispersion A (colour former dispersion) was prepared by grinding 20 parts by weight of 3-N-n-dibutylamino-6-methyl-7-anilinofluorane (ODB-2) with 33 parts by weight of a 15% aqueous solution of Ghosenex™ L-3266 (sulfonated polyvinyl alcohol, Nippon Ghosei) in a bead mill.

An aqueous dispersion B (colour developer dispersion) was prepared by grinding 40 parts by weight of the colour developer together with 66 parts by weight of a 15% aqueous solution of Ghosenex™ L-3266 in the bead mill.

An aqueous dispersion C (sensitisation agent dispersion) was prepared by grinding 40 parts by weight of sensitisation agent with 33 parts by weight of a 15% aqueous solution of Ghosenex™ L-3266 in a bead mill.

All dispersions produced by grinding had a mean particle size D$_{(4,3)}$ of from 0.80 to 1.20 µm. The particle size distribution of the dispersions was measured by laser diffraction using a Coulter LS230 apparatus from Beckman Coulter.

A dispersion D (slip additive dispersion) was a 20% zinc stearate dispersion consisting of 9 parts by weight of Zn stearate, 1 part by weight of Ghosenex™ L-3266, and 40 parts by weight of water.

Pigment P was a 72% coating kaolin suspension (Lustra® S, BASF).

The binder consisted of a 10% aqueous polyvinyl alcohol solution (Mowiol 28-99, Kuraray Europe).

The heat-sensitive suspension to be applied was prepared by mixing, under stirring, of 1 part A, 1 part B, 1 part C, 56 parts D, 146 parts pigment P, and 138 parts binder solution (all parts by weight) under consideration of the order of introduction B, D, C, P, A, binder, and by bringing the mixture with water to a solids content of approximately 25%.

The heat-sensitive coating suspensions thus obtained were used to produce composite structures of paper carrier and thermal reaction layer.

The thermal recording materials were assessed as described hereinafter (see Tables 3, 4 and 5).

(1) Dynamic Colour Density:

The papers (strips 6 cm wide) were thermally printed with use of an Atlantek 200 test printer (Atlantek, USA) with a Kyocera printhead of 200 dpi and 560 ohms with an applied voltage of 20.6 V and a maximum pulse width of 0.8 ms with a chequered pattern with 10 energy gradations. The image density (optical density (o.D.)) was measured using a SpectroEye densitometer from X-Rite at an energy stage of 0.25 and 0.45 mJ/dot. The measurement uncertainty of the o.D. values was estimated at 52%.

(2) Static Colour Density (Starting Temperature):

The recording material sheet was pressed against a series of thermostatically controlled metal dies heated to different temperatures with a press-on pressure of 0.2 kg/cm$^2$ and a contact time of 5 sec. (thermal tester TP 3000QM, Maschinenfabrik Hans Rychiger AG, Stefflisburg, Switzerland). The image density (optical density) of the images thus produced was measured using a SpectroEye densitometer from X-Rite.

The static starting point, according to definition, is the lowest temperature at which an optical density of 0.2 is achieved. The accuracy of the measurement method was ≤0.5° C.

(3) Resistance Test of the Printed Image:

a) Plasticiser Resistance:

A plasticiser-containing cling film (PVC film with 20 to 25% dioctyl adipate) was brought into contact with the sample of the thermal recording paper, which had been dynamically recorded in accordance with the method under (1), avoiding folds and inclusions of air, then rolled up into a roll and stored for 16 hours. One sample was stored at room temperature (20 to 22° C.), and a second sample was stored at 40° C. After removal of the film, the image density (o.D.) was measured and set in relation to the corresponding image density values before the action of the plasticiser in accordance with formula (Eq. 1).

b) Resistance to Adhesive:

A strip of transparent self-adhesive tape from Tesa (tesafilm® crystal-clear, #57315), and separately therefrom a strip of packaging adhesive tape from Tesa (#04204) were adhered to the sample of the thermal recording paper, which had been dynamically recorded in accordance with the method under (1), avoiding folds and inclusions of air. After storage at room temperature (20 to 22° C.), the image density (o.D.) was measured after 24 hours and after 7 days—through the particular adhesive tape—and, in accordance with the formula (Eq. 1), was set in relation to the similarly determined image density values of a freshly adhered specimen.

$$\% \text{ remaining image density} = \frac{\text{image density after test}}{\text{image density before test}} * 100 \quad \text{(Eq. 1)}$$

The scattering of the % values calculated by (Eq. 1) was ≤±2 percentage points.

Tables 3 to 5 summarise the evaluation of the produced recording materials.

TABLE 3

Image density (optical density with an energisation energy of 0.25 and 0.45 mJ/dot) and starting temperature (starting point) of the colour developer

| Colour developer | o.D. (0.25 mJ/dot) | o.D. (0.45 mJ/dot) | Starting point (° C.) |
|---|---|---|---|
| I | 1.16 | 1.22 | 81 |
| II | 1.20 | 1.24 | 76 |
| III | 1.13 | 1.24 | 76 |
| IV | 1.19 | 1.20 | 71 |
| V | 1.17 | 1.20 | 76 |
| VII | 1.15 | 1.23 | 86 |
| VIII | 1.20 | 1.23 | 73 |
| X | 1.24 | 1.30 | 82 |
| XIII | 1.14 | 1.20 | 79 |
| XXIII | 1.16 | 1.26 | 82 |
| XXIV | 1.09 | 1.26 | 82 |
| Z | 1.19 | 1.24 | 86 |
| PF201 | 1.19 | 1.23 | 76 |

TABLE 4

Image density (optical density with an energisation energy of 0.25 and 0.45 mJ/dot) depending on the substitution pattern of the colour developer

| Colour developer | Relative position of the sulfonamide and urea groups | o.D. (0.25 mJ/dot) | o.D. (0.45 mJ/dot) |
|---|---|---|---|
| II | 1.2 | 1.20 | 1.24 |
| XIV | 1.3* | 1.05 | 1.16 |
| XVII | 1.4* | 0.55 | 1.20 |
| III | 1.2 | 1.13 | 1.24 |
| XV | 1.3* | 1.00 | 1.17 |
| XVIII | 1.4* | 0.84 | 1.19 |
| IV | 1.2 | 1.19 | 1.20 |
| XVI | 1.3* | 0.93 | 1.16 |
| XIX | 1.4* | 0.57 | 1.19 |

*comparative examples

TABLE 5

Resistance of the printed image of the colour developer

| Colour developer | Tesa adhesive tape* | | | | Plasticiser film* | |
|---|---|---|---|---|---|---|
| | 24 h | | 7 days | | 16 h | |
| | #57315 | #04204 | #57315 | #04204 | R.T. | 40° C. |
| I | 83 | 47 | 16 | 14 | 98 | 88 |
| II | 74 | 43 | 34 | 16 | 99 | 77 |
| III | 71 | 49 | 37 | 19 | 97 | 83 |
| IV | 71 | 42 | 32 | 14 | 98 | 89 |
| V | 67 | 38 | 18 | 11 | 97 | 68 |
| VII | 70 | 40 | 33 | 15 | 98 | 84 |
| VIII | 71 | 46 | 23 | 15 | 88 | 67 |
| X | 75 | 44 | 25 | 20 | 99 | 90 |
| XIII | 74 | 37 | 33 | 16 | 100 | 93 |
| XXIII | 92 | 90 | 74 | 65 | 94 | 92 |
| XXIV | 91 | 89 | 68 | 61 | 100 | 95 |
| Z | 60 | 35 | 12 | 13 | 83 | 17 |
| PF201 | 73 | 46 | 32 | 16 | 97 | 78 |

*Percentage of remaining image density in accordance with Eq. 1

It can be seen from the examples above that the heat-sensitive recording material of the present invention presents the following advantageous properties especially:

(1) The recorded image of the heat-sensitive recording materials based on the colour developers according to the invention has print densities (optical densities) comparable to those of the comparison specimens from the prior art (Table 3).

(2) The heat-sensitive recording materials based on colour developers with the substitution pattern according to the invention (1,2 position (ortho position) of the relevant functional groups) have significantly higher print densities than the recording materials based on colour developers with alternative substitution patterns (1,3 and 1,4 position of the relevant functional groups); see II with XIV and XVII, III with XV and XVIII and IV with XVI and XIX (Table 4).

(3) The temperature from which a visually noticeable greying of the recording materials according to the invention occurred (static starting point) satisfies the requirements of marketable heat-sensitive recording materials (Table 3).

(4) The image resistance after the action of hydrophobic agents (adhesives, plasticisers) is better than or comparable to the corresponding performance of the known non-phenolic colour developer materials according to the prior art (Table 5).

(5) A heat-sensitive recording material of high quality in respect of key application properties can be obtained with the colour developers according to the invention. No recording material based on known colour developers has a comparable balanced performance profile across all tested properties.

The invention claimed is:

1. A heat-sensitive recording material, comprising a carrier substrate and a heat-sensitive colour-forming layer, which contains at least one colour former and at least one phenol-free colour developer, wherein the at least one colour developer is the compound of formula (I):

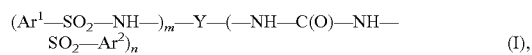

$$(Ar^1—SO_2—NH—)_m—Y—(—NH—C(O)—NH—SO_2—Ar^2)_n \qquad (I),$$

wherein Y is at least one benzene group substituted (m+n) times, and Y is substituted in such a way that at least one $Ar_2$—$SO_2$—NH—C(O)—NH group is in the ortho position with respect to at least one $Ar^1$—$SO_2$—NH group, wherein $Ar^2$ is an unsubstituted phenyl group or a monosubstituted phenyl group and, wherein $Ar^1$ is an unsubstituted, substituted or monosubstituted phenyl group, or an unsubstituted or substituted 2-naphthy group, which is substituted with a $C_1$-$C_5$ alkyl, an alkenyl, an alkynyl, a benzyl, an RO, a halogen, a formyl, an ROC, an $RO_2C$, a CN, an $NO_2$, an R—$SO_2O$, an RO—$SO_2$, an R—NH—$SO_2$, an R—$SO_2$—NH, an R—NH—CO—NH, an R—$SO_2$—NH—CO—NH, an R—NH—CO—NH—$SO_2$ or an R—CO—NH group, wherein R is a $C_1$-$C_5$ alkyl, an alkenyl, an alkynyl, a phenyl, a tolyl or a benzyl group.

2. The heat-sensitive recording material according to claim 1, wherein the at least one colour former is a dye of triphenylmethane, fluorane, azaphthalide and/or fluorene.

3. The heat-sensitive recording material according to claim 1, wherein, besides the compound of formula (I), one or more further non-phenolic colour developers are also present.

4. The heat-sensitive recording material according to claim 1, wherein the compound of formula (I) is present in an amount of from approximately 3 to approximately 35% by weight in relation to the total solids content of the heat-sensitive layer.

5. The heat-sensitive recording material according to claim 1, wherein the heat-sensitive colour-forming layer contains a urea urethane compound of general formula (II)

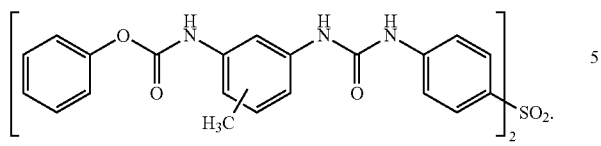
(II)

6. The heat-sensitive recording material according to claim 1, wherein the compound of formula (I) is present in an amount of from approximately 10 to approximately 25% by weight in relation to the total solids content of the heat-sensitive layer.

7. The heat-sensitive recording material according to claim 1, wherein $Ar^1$ is a phenyl group.

8. The heat-sensitive recording material according to claim 1, wherein $Ar^1$ is a $C_1$-$C_5$ alkyl-substituted phenyl group.

9. A method for producing a heat-sensitive recording material according to claim 1, wherein an aqueous suspension containing the starting materials of the heat-sensitive colour-forming layer is applied to a carrier substrate and dried, wherein the aqueous suspension to be applied has a solids content of from approximately 20 to approximately 75% by weight, and is applied using the curtain-coating process at an operating speed of the coating facility of at least approximately 400 m/min.

10. A heat-sensitive recording material obtainable by the method according to claim 9.

* * * * *